United States Patent
Braun

(10) Patent No.: US 6,554,871 B2
(45) Date of Patent: Apr. 29, 2003

(54) OXIDATIVE HAIR DYE PRECURSOR COMPOSITIONS CONTAINING 4-5-DIAMINOPYRAZOLE, 5-AMINO-2-METHYLPHENOL AND M-PHENYLENEDIAMINE COMPOUNDS AND METHOD OF DYEING HAIR

(75) Inventor: Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 50 days.

(21) Appl. No.: 09/788,945

(22) Filed: Feb. 20, 2001

(65) Prior Publication Data
US 2001/0009044 A1 Jul. 26, 2001

Related U.S. Application Data

(63) Continuation-in-part of application No. 09/091,203, filed as application No. PCT/EP97/05341 on Sep. 27, 1997, now abandoned.

(30) Foreign Application Priority Data

Oct. 18, 1996 (DE) .......................................... 196 43 059

(51) Int. Cl.[7] .................................................. A61K 7/13
(52) U.S. Cl. ...................... 8/409; 8/423; 8/411; 8/412; 8/416
(58) Field of Search .............................. 8/409, 423, 411, 8/412, 416, 421

(56) References Cited

U.S. PATENT DOCUMENTS

| 5,061,289 | A | * | 10/1991 | Clausen et al. |
| 5,637,115 | A | * | 6/1997 | Balzer et al. |
| 5,718,731 | A | * | 2/1998 | Loewe et al. |

* cited by examiner

*Primary Examiner*—Margaret Einsmann
(74) *Attorney, Agent, or Firm*—Michael J. Striker

(57) ABSTRACT

The oxidation dye precursor-containing composition for oxidative dyeing of hair, includes from 0.1 to 10% by weight of a combination of at least one 4,5-diaminopyrazole compound selected from the group consisting of 4,5-diamino-1-methyl-1H-pyrazole, 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole; at least one 5-amino-2-methylphenol compound selected from the group consisting of 5-amino-2-methylphenol, 5-[(2'-hydroxyethyl)amino]-2-methylphenol and 5-methyl-amino-2-methyl-phenol; and at least one m-phenylenediamine compound selected from the group consisting of m-phenylenediamine, 2,4-diamino-1-(2'-hydroxyethoxy)benzene, 2,4-diamino-1-(2',3'-dihydroxypropoxy)benzene, 1,3-bis-(2',4'-diaminophenoxy) propane, 2-amino-4-[(2'-hydroxyethyl)amino]anisole and 1,5-bis-(2'-hydroxyethoxy)-2,4-diaminobenzene. The composition is advantageously mixed with an oxidant to form a ready-to-apply hair dyeing mixture for dyeing hair.

12 Claims, No Drawings

OXIDATIVE HAIR DYE PRECURSOR COMPOSITIONS CONTAINING 4-5-DIAMINOPYRAZOLE, 5-AMINO-2-METHYLPHENOL AND M-PHENYLENEDIAMINE COMPOUNDS AND METHOD OF DYEING HAIR

CROSS-REFERENCE

This is a continuation-in-part of U.S. patent application, Ser. No. 09/091,203, filed Jun. 10, 1998, now abandoned, which is a 371 of PCT/EP97/05341, filed Sep. 27, 1997.

BACKGROUND OF THE INVENTION

1. Field of the Invention

The present invention relates to a composition for dyeing keratin fibers, especially human hair, which contains a combination of at least one 4,5-diaminopyrazole, one m-aminophenol and one m-phenylenediamine. It also relates to a method of dyeing keratin fibers, especially hair, performed by mixing the aforementioned composition with an oxidant, applying the resulting mixture to the keratin fibers, and, after a certain acting time, washing the mixture out with water and a shampoo.

2. Prior Art

For a certain group of applications, there is a demand for compositions which are capable of dyeing the hair in copper-colored, chestnut-brown to red shades. This demand is currently being satisfied by putting hair dyes with a content of certain oxidative dye-precursor compounds on the market. For example, in German Published, Non-Examined Patent Application DE-OS 36 10 396, to produce neutral red tints, a method using a combination of 5-amino-2-methylphenol, 4-amino-3-methylphenol and 1,4-diaminobenzene and/or 2,5-diaminotoluene is described. In European Published Patent Application EP 0 634 162, examples are given for combining 5-amino-2-methylphenol and its n-substituted derivatives, 4-amino-2-methylphenol, 4-amino-3-methylphenol, 4-amino-2-hydroxymethylphenol, and certain m-phenylenediamine derivatives.

The resistance of the hair colorings produced by the prior art to the effects of light, washing, weathering, sweat, and other hair treatments is unsatisfactory, however.

SUMMARY OF THE INVENTION

It is an object of the present invention to provide an improved oxidative dye-precursor composition, especially for dyeing hair, which provides dyed hair colors having an improved resistance to the effects of light, washing, weathering, sweat and the like.

It has now been surprisingly discovered that the above-described disadvantages are avoided, or at least reduced, when an oxidative dye-precursor composition including the following combination of dye-precursor compounds is employed in a method of oxidative hair dyeing to produce colors in the reddish color range.

The oxidative dye-precursor composition according to the invention comprises a combination of at least one 4,5-diaminopyrazole compound selected from the group consisting of 4,5-diamino-1-methyl-1H-pyrazole, 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole;

at least one 5-amino-2-methylphenol compound selected from the group consisting of 5-amino-2-methylphenol, 5-[(2'-hydroxyethyl)amino]-2-methylphenol and 5-methylamino-2-methylphenol; and at least one m-phenylenediamine compound selected from the group consisting of m-phenylenediamine, 2,4-diamino-1-(2'-hydroxyethoxy)benzene, 2,4-diamino-1-(2',3'-dihydroxypropoxy)benzene, 1,3-bis-(2',4'-diaminophenoxy)propane, 2-amino-4-[(2'-hydroxyethyl)amino]anisole and 1,5-bis-(2'-hydroxyethoxy)-2,4-diaminobenzene.

The synthesis and use of the above-mentioned 4,5-diaminopyrazole compounds in oxidative hair dyes is known in principle from published, non-examined German Patent Application DE-OS 42 34 885. The novel combinations with hair color precursors, however, have surprising advantages with regard to the stability of the hair colors achieved.

DESCRIPTION OF PREFERRED EMBODIMENTS

The 4,5-diaminopyrazole compounds preferred for the composition according to the invention consist of 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole.

The 5-amino-2-methylphenol compounds preferred for the composition according to the invention consist of 5-amino-2-methylphenol and 5-[(2'-hydroxyethyl)amino]-2-methylphenol.

The substituted m-phenylenediamine compounds preferred for the composition according to the invention consist of 2,4-diamino-1-(2'-hydroxyethoxy)benzene, 1,3-bis-(2',4'-diaminophenoxy)propane and 2-amino-4-[(2'-hydroxyethyl)amino]anisole.

To round out the outcome of dyeing and to create special color effects, other oxidative dye precursors, such as derivatives of p-phenylenediamine, for example 2-(2',5'-diaminophenyl)ethanol, resorcinol derivatives, such as resorcinol or 4-chloro-resorcinol, amino and hydroxy derivatives of 1,3-benzodioxol, naphthalene derivatives, such as 1-hydroxynaphthalene, 1,5-dihydroxynaphthalene, or 1,7-dihydroxynaphthalene, as well as direct dyes, such as 2-amino-4,6-dinitrophenol, 2-ethylamino-4,6-dinitrophenol, 2-(2'-hydroxyethyl)amino]-4,6-dinitrophenol, 2-amino-6-chloro-4-nitrophenol, or 2-chloro-6-ethylamino-4-nitrophenol, can be added to the aforementioned dye precursor combination.

The above-described combination according to the invention of oxidative dye precursor compounds and optionally direct-dyeing dye compounds are applied e.g. to hair for dyeing purposes in a suitable oxidation dye-precursor-containing composition.

The subject of the present application therefore also relates to means for oxidatively dyeing hair prepared by mixing the oxidation dye-precursor-containing composition of the invention with an oxidant immediately prior to use.

The oxidation dye-precursor-containing composition according to the invention contains the above-described combinations according to the invention of oxidative hair dye precursor compounds and optionally direct-dyeing dye compounds either per se or in the form of biocompatible salts, for instance in the form of hydrochlorides, sulfates or tartrates, or in the case of phenols in the form of alkali phenolates.

The total amount of oxidation-dye precursor compounds in the composition according to the invention is from 0.1 to 10 weight %, preferably 0.2 to 6 weight %. The concentration of the individual oxidation-dye precursor compounds ranges from 0.01 to 5 weight %, and preferably 0.1 to 4 weight %.

Typical cosmetic additives can also be contained in the oxidation dye-precursor-containing composition. Examples of these additives include antioxidants, such as ascorbic acid, thioglycolic acid or sodium sulfite; perfume oils; complexing agents; wetting agents; emulsifiers; thickeners; conditioners, and others.

The form of preparation for the oxidation dye-precursor-containing composition and also for the oxidative dye mixture for hair that is ready-to-apply may, for example, be a solution, and in particular an aqueous or aqueous-alcohol solution. The particularly preferred forms of the preparation, however, are a cream, gel, or emulsion. Their composition represents a mixture of the dye ingredients with additives typical for such preparations.

Conventional additives in solutions, creams, emulsions, or gels are, for example, solubilizers with water, low aliphatic alcohols, such as ethanol, n-propanol and isopropanol, or glycols, such as glycerol and 1,2-propylene glycol, and also neutralizers or emulsifiers selected from the anionic, cationic, amphoteric or non-ionic classes of surfactants, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters; thickeners, such as higher fatty alcohols, starch or cellulose derivatives; and petrolatum (Vaseline®), paraffin oil and fatty acids, as well as conditioners such as cationic resins, lanolin derivatives, cholesterol, pantothenic acid and betaine. The aforementioned ingredients are used in the customary quantities appropriate for their purposes, for example the neutralizers and emulsifiers are included in the composition of the invention in a concentration of approximately 0.5 to 30 weight % (referred to the total amount of the oxidation dye-precursor-containing composition); the thickeners in a quantity of approximately 0.1 to 25 weight % (referred to the total amount of the oxidation dye-precursor-containing composition) and the conditioners in a concentration of approximately 0.1 to 5.0 weight % (referred to the total amount of the oxidation dye-precursor-containing composition).

The ready-to-use hair dyeing mixture in accordance with the invention is prepared immediately before application by mixing the oxidation dye-precursor-containing composition with a liquid oxidant.

The oxidation dye-precursor-containing composition and the oxidant in this case are mixed together in a weight ratio of 5:1 to 1:3, with a weight ratio of 1:1 to 1:2 being especially preferred.

In the mixing of the preferably alkaline oxidation dye-precursor-containing composition, the pH-value of the ready-to-apply hair dyeing mixture according to the invention is adjusted by means of the usually acidic oxidant to a pH value that is varied by means of the quantities of alkali in the oxidation dye-precursor-containing composition and of acid in the oxidant, and by the mixture ratio. The pH-value of the ready-to-apply hair dyeing mixture may be from 3 to 11, and preferably 5 to 9.

For adjusting the pH-value of the oxidation dye-precursor-containing composition and the oxidant, one can use organic and inorganic acids, such as phosphoric acid, ascorbic acid and lactic acid, or alkalis, such as monoethanolamine, triethanolamine, 2-amino-2-methyl-1-propanol, ammonia, sodium hydroxide, potash lye, or tris-(hydroxymethyl)-aminomethane, depending on the desired pH-value.

For use in oxidative hair dyeing, the above-described oxidation dye-precursor-containing composition is mixed with an oxidant immediately before use, and an appropriate amount of the ready-to-apply oxidative hair dyeing mixture obtained that is suitable for the hair dyeing treatment is applied to the hair, generally from about 60 to 200 grams, depending on the fullness of the hair.

As an oxidant, primarily hydrogen peroxide, or its addition compounds of uric acid, melamine, or sodium bromate, in the form of a 1 to 12%, and preferably a 6% aqueous solution, can be employed. Hydrogen peroxide is preferred as the oxidant.

The hair dyeing mixture in accordance with the invention is left to act on the hair for approximately 10 to 45 minutes at 15 to 50° C., preferably for 30 minutes; the hair is then rinsed with water and dried. If necessary, the hair may be washed with a shampoo after rinsing, and optionally may be re-rinsed with a weak organic acid, such as citric acid or tartaric acid. The hair is then dried.

The following examples are intended to explain the invention in further detail, without limiting it to these examples.

EXAMPLES

Examples 1–6

Hair Dye Solutions With an Alkaline pH Value

The following dye solution is prepared:

| | |
|---|---|
| 10.0 g | isopropanol |
| 10.0 g | lauryl alcohol diglycol ether sulfate sodium salt (28% aqueous solution) |
| 10.0 g | ammonia, 25% aqueous solution |
| 0.3 g | ascorbic acid |
| X g | color precursors per Table 1 |
| water, | fully delsalinated, in an amount to make 100.0 g |

Prior to application, 10 g of hair dye solution are mixed with 10 g of hydrogen peroxide solution (6% solution in water). The oxidative hair dyeing mixture obtained is applied to tiny strands of hair. After an acting time of 30 minutes at 40° C., the hair is rinsed with water, shampooed, and dried.

TABLE I

COMPOSITION OF HAIR DYE-PRECURSOR SOLUTIONS TESTED IN GRAMS

| | Composition No. | | | | | |
|---|---|---|---|---|---|---|
| | 1 | 2 | 3 | 4 | 5 | 6 |
| 4,5-diamino-1-(1'-methyl-ethyl)-1H-pyrazole sulfate | 1.5 | — | 2.1 | — | 1.9 | — |
| 4,5-diamino-1-(2'-hydroxy-ethyl)-1H-pyrazole sulfate | — | 2.0 | — | 2.6 | — | 3.5 |
| 5-amino-2-methylphenol | 1.0 | 1.3 | 0.6 | 0.6 | — | 0.3 |
| 5-[(2'-hydroxyethyl)- | — | — | — | — | 0.8 | 0.5 |

TABLE I-continued

COMPOSITION OF HAIR DYE-PRECURSOR SOLUTIONS TESTED IN GRAMS

|  | Composition No. | | | | | |
| --- | --- | --- | --- | --- | --- | --- |
|  | 1 | 2 | 3 | 4 | 5 | 6 |
| amino]-2-methylphenol | | | | | | |
| 2,4-diamino-1-(2'-hydroxy-ethoxy)-benzene dichloride | — | 0.3 | 1.2 | — | 1.2 | 0.1 |
| 1,3-bis-(2',4'-diaminophenoxy)-propane tetrahydrochloride | 0.3 | — | — | — | — | 0.5 |
| 2-amino-4-[(2'-hydroxyethyl)-amino anisole sulfate | 0.3 | 0.4 | — | — | — | 1.2 |
| 1,5-bis(2'-hydroxyethoxy)-2,4-diamimo-benzene hydrochloride | — | — | — | 1.5 | — | — |

Colors produced by dyeing bleached hair: 1) bordeaux, 2) wine red, 3)cyclamen, 4) cyclamen, 5) cyclamen, 6) trendy reddish-brown Example 7

Oxidation Hair Dye-Precursor Composition in Cream Form

| 0.52 g | 2,5-diaminophenylethyl alcohol sulfate |
| --- | --- |
| 0.95 g | 4,5-diamino-(2-hydroxyethyl)-1H-pyrazole sulfate |
| 0.24 g | resorcinol |
| 0.30 g | m-aminophenol |
| 0.24 g | 2-amino-4-(2'-hyd roxyethyl)aminoanisole sulfate |
| 0.20 g | 5-amino-2-methylphenol |
| 0.05 g | 2-amino-6-chloro-4-nitrophenol |
| 0.12 g | 1-naphthol |
| 15.00 g | cetyl alcohol |
| 3.50 g | sodium lauryl alcohol diglycol ether sulfate, 28% aqueous solution |
| 3.00 g | ammonia, 25% aqueous solution |
| 0.30 g | sodium sulfite, anhydrous |
| 75.58 g | water |
| 100.00 g | |

10 g of this hair dye are mixed shortly before use with 10 ml of hydrogen peroxide solution (6% concentration). Then the mixture is applied to blond virgin hair and left to act for 30 minutes at 40° C. After that, the hair is rinsed with water and dried. The hair has been given a reddish-brown color.

Example 8

Oxidation Hair Dye-Precursor Composition in Gel Form

| 1.5 g | 5-amino-2-methylphenol |
| --- | --- |
| 1.0 g | 4,5-diamino-1-(2'-hydroxyethyl)-1H-pyrazole sulfate |
| 0.6 g | 2,5-diaminotoluene sulfate |
| 0.5 g | 2-chloro-6-ethylamino-4-nitrophenol |
| 0.4 g | sodium hydroxide, solid |
| 0.6 g | ascorbic acid |
| 7.0 g | isopropanol |
| 15.0 g | oleic acid |
| 10.0 g | ammonia, 25% aqueous solution |
| 62.5 g | water |
| 100.0 g | |

Shortly before use, 50 g of this hair dye is mixed with 50 ml of hydrogen peroxide solution (6% concentration), and the mixture is left to act on blond human hair for 30 minutes. After that, it is rinsed with water and then dried.

A reddish-brown hair color is obtained.

Example 9

Acidic Oxidation Hair Dye-Precursor Solution

| 0.30 g | 2-(2',5'-diaminophenyl)ethanol sulfate |
| --- | --- |
| 0.18 g | 4-chlororesorcinol |
| 0.30 g | 4,5-diamino-1-(2'-hydroxyethyl)-1H-pyrazole sulfate |
| 0.30 g | 1-naphthol |
| 0.30 g | ascorbic acid |
| 0.20 g | sodium lauryl ether sulfate |
| 0.22 g | ammonia, 25% aqueous solution |
| 98.12 g | water |
| 100.00 g | |

The pH value of the oxidation dye-precursor composition is adjusted to a pH value of 6.8 with dilute phosphoric acid or a dilute ammonia solution.

Immediately before use, 20 g of the hair coloring solution are mixed with 20 g of a 6% aqueous hydrogen peroxide solution (pH 6.8), and the oxidative hair dyeing mixture obtained (pH=6.8) is applied to bleached hair. After an action time of 30 minutes at room temperature, the hair is rinsed with water and dried.

The hair thus treated is colored a reddish-violet shade.

While the invention has been illustrated and described as embodied in oxidation hair dye precursor compositions and methods of dyeing hair with same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

I claim:

1. An oxidation dye precursor-containing composition for oxidative dyeing of hair, said composition containing a combination of at least one 4,5-diaminopyrazole compound selected from the group consisting of 4,5-diamino-1-methyl-1H-pyrazole, 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole;

at least one 5-amino-2-methylphenol compound selected from the group consisting of 5-amino-2-methylphenol, 5-[(2'-hydroxyethyl)amino]-2-methylphenol and 5-methylamino-2-methylphenol; and at least one m-phenylenediamine compound selected from the group consisting of m-phenylenediamine, 2,4-diamino-1-(2'-hydroxyethoxy)benzene, 2,4-diamino-1-(2',3'-dihydroxypropoxy)benzene, 1,3-bis-(2',4'-diaminophenoxy)propane, 2-amino-4-[(2'-hydroxyethyl)amino]anisole and 1,5-bis-(2'-hydroxyethoxy)-2,4-diaminobenzene.

2. The oxidation dye precursor-containing composition as defined in claim 1, further comprising at least one oxidative dye precursor compound selected from the group consisting of p-phenylenediamine, substituted p-phenylenediamine compounds, resorcinol, substituted resorcinol compounds, substituted 1,3-benzodioxol compounds and substituted naphthalene compounds.

3. The oxidation dye precursor-containing composition as defined in claim 1, further comprising at least one direct-dyeing compound.

4. The oxidation dye precursor-containing composition as defined in claim 1, further comprising a cosmetic vehicle for said at least one 4,5-diaminopyrazole compound; said at least one 5-amino-2-methylphenol compound and said at least one m-phenylene-diamine compound.

5. The oxidation dye precursor-containing composition as defined in claim 1, wherein each of said at least one 4,5-diaminopyrazole compound; said at least one 5-amino-2-methylphenol compound and said at least one m-phenylenediamine compound is present in an amount of from 0.01 to 5% by weight and a total amount of said combination present is from 0.1 to 10% by weight.

6. The oxidation dye precursor-containing composition as defined in claim 1, further comprising at least one cosmetic additive ingredient.

7. An oxidation dye precursor-containing composition for oxidative dyeing of hair, said composition containing a combination of
at least one 4,5-diaminopyrazole compound selected from the group consisting of 4,5-diamino-1-ethyl-1H-pyrazole, 4,5-diamino-1-isopropyl-1H-pyrazole, 4,5-diamino-1-(2-hydroxyethyl)-1H-pyrazole, 4,5-diamino-1-benzyl-1H-pyrazole and 4,5-diamino-1-(4'-methylbenzyl)-1H-pyrazole;
at least one 5-amino-2-methylphenol compound selected from the group consisting of 5-amino-2-methylphenol and 5-[(2'-hydroxyethyl)amino]-2-methylphenol; and
at least one m-phenylenediamine compound selected from the group consisting of 2,4-diamino-1-(2'-hydroxyethoxy)benzene, 1,3-bis-(2',4'-diaminophenoxy)propane and 2-amino-4-[(2'-hydroxyethyl)amino]anisole.

8. A ready-to-apply hair dyeing mixture made by mixing an oxidation dye precursor containing composition with an oxidant in a ratio of from 5:1 to 1:3, said oxidation dye precursor-containing composition containing a combination of
at least one 4,5-diaminopyrazole compound selected from the group consisting of 4,5-diamino-1-methyl-1H-pyrazole, 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole;
at least one 5-amino-2-methylphenol compound selected from the group consisting of 5-amino-2-methylphenol, 5-[(2'-hydroxyethyl)amino]-2-methylphenol and 5-methylamino-2-methylphenol; and
at least one m-phenylenediamine compound selected from the group consisting of m-phenylenediamine, 2,4-diamino-1-(2'-hydroxyethoxy)benzene, 2,4-diamino-1-(2',3'-dihydroxypropoxy)benzene, 1,3-bis-(2',4'-diaminophenoxy)propane, 2-amino-4-[(2'-hydroxyethyl)amino]anisole and 1,5-bis-(2'-hydroxyethoxy)-2,4-diaminobenzene.

9. The ready-to-apply hair dyeing mixture as defined in claim 8, having a pH from 3 to 11.

10. A ready-to-apply hair dyeing mixture made by mixing an oxidation dye precursor containing composition with an oxidant in a ratio of from 5:1 to 1:3, said oxidation dye precursor-containing composition containing a combination of
at least one 4,5-diaminopyrazole compound selected from the group consisting of 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole;
at least one 5-amino-2-methylphenol compound selected from the group consisting of 5-amino-2-methylphenol and 5-[(2'-hydroxyethyl)amino]-2-methylphenol; and
at least one m-phenylenediamine compound selected from the group consisting of 2,4-diamino-1-(2'-hydroxyethoxy)benzene, 1,3-bis-(2',4'-diaminophenoxy)propane and 2-amino-4-[(2'-hydroxyethyl)amino]anisole.

11. A method of dyeing hair, said method comprising the steps of:
a) providing an oxidation dye precursor-containing composition containing a combination of at least one 4,5-diaminopyrazole compound selected from the group consisting of 4,5-diamino-1-methyl-1H-pyrazole, 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole; at least one 5-amino-2-methylphenol compound selected from the group consisting of 5-amino-2-methylphenol, 5-[(2'-hydroxyethyl)amino]-2-methylphenol and 5-methyl-amino-2-methylphenol; and at least one m-phenylenediamine compound selected from the group consisting of m-phenylenediamine, 2,4-diamino-1-(2'-hydroxyethoxy)benzene, 2,4-diamino-1-(2',3'-dihydroxypropoxy)benzene, 1,3-bis-(2',4'-diaminophenoxy)propane, 2-amino-4-[(2'-hydroxyethyl)amino]anisole and 1,5-bis-(2'-hydroxyethoxy)-2,4-diaminobenzene;
b) mixing said oxidation dye precursor-containing composition of step a) with an oxidant in a ratio of from 5:1 to 1:3 to form a ready-to-apply hair dyeing mixture;
c) applying the ready-to-apply hair dyeing mixture to the hair to be dyed and allowing the ready-to-apply hair dyeing mixture to act on the hair for from 10 to 45 minutes at a temperature of from 15 to 50° C.; and
d) subsequently rinsing the hair with water, washing with a shampoo as needed and then drying the hair.

12. A method of dyeing hair, said method comprising the steps of:
a) providing an oxidation dye precursor-containing composition containing a combination of at least one 4,5-diaminopyrazole compound selected from the group consisting of 4,5-diamino-1-ethyl-1H-pyrazole, 4,5-diamino-1-isopropyl-1H-pyrazole, 4,5-diamino-1-(2'-hydroxyethyl)-1H-pyrazole, 4,5-diamino-1-benzyl-1H-pyrazole and 4,5-diamino-1-(4'-methylbenzyl)-1H-pyrazole; at least one 5-amino-2-methylphenol compound selected from the group consisting of 5-amino-2-methylphenol and 5-[(2'-hydroxy-ethyl)amino]-2-methyl-phenol; and at least one m-phenylenediamine compound selected from the group consisting of 2,4-diamino-1-(2'-hydroxyethoxy)benzene, 1,3-bis-(2',4'-diamino-phenoxy)propane and 2-amino-4-[(2'-hydroxyethyl)amino]anisole;

b) mixing said oxidation dye precursor-containing composition of step a) with an oxidant in a ratio of from 5:1 to 1:3 to form a ready-to-apply hair dyeing mixture having a pH of from 3 to 11;

c) applying the ready-to-apply hair dyeing mixture to the hair to be dyed and allowing the ready-to-apply hair dyeing mixture to act on the hair for from 10 to 45 minutes at a temperature of from 15 to 50° C.; and d) subsequently rinsing the hair with water, washing with a shampoo as needed and then drying the hair.

* * * * *